United States Patent [19]

Fink et al.

[11] Patent Number: 5,359,640
[45] Date of Patent: Oct. 25, 1994

[54] X-RAY MICRO DIFFRACTOMETER SAMPLE POSITIONER

[75] Inventors: Juergen Fink, Elcheshein-Illingen; Rolf Schipper, Karlsruhe, both of Fed. Rep. of Germany; Kingsley Smith; Richard Ortega, both of Madison, Wis.

[73] Assignee: Siemens Industrial Automation, Inc., Alpharetta, Ga.

[21] Appl. No.: 104,311

[22] Filed: Aug. 10, 1993

[51] Int. Cl.$^5$ .............................. G01N 23/20
[52] U.S. Cl. ......................... 378/79; 378/70; 378/81; 378/206
[58] Field of Search ............ 378/70, 71, 79, 205, 378/206, 81

[56] References Cited
U.S. PATENT DOCUMENTS 5,127,039 6/1992 Hesch ................... 378/81

Primary Examiner—David P. Porta
Assistant Examiner—Don Wong
Attorney, Agent, or Firm—Donald M. Boles

[57] ABSTRACT

An X-ray diffractometer having a simple yet accurate means for locating the surface of the sample to be examined with respect to the zero point of the X-ray (RS) is disclosed. Briefly stated, a laser (LA) and camera (KA) are positioned at preferably 90° with respect to each other such that the intersection of the optical axis of the camera and the laser passes through the zero point of the diffractometer. In this fashion, the camera will see at its center, the zero point of the X-ray despite the fact that the X-ray is of course invisible to the naked eye. Accordingly, by movement of the sample (P) with respect to this camera image, the true and correct zero point of the X-ray with respect to the surface of the sample to be examined may be determined without the need for experimental and unnecessary X-ray or examination runs being taken.

6 Claims, 2 Drawing Sheets

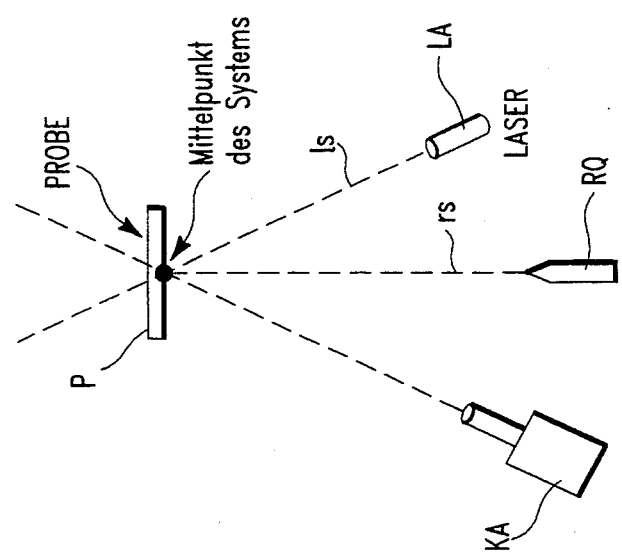
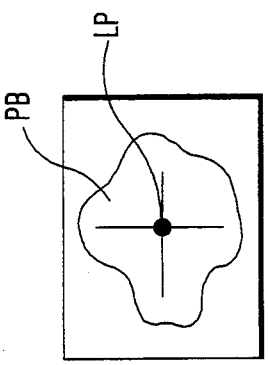
FIG. 3a
FIG. 3b
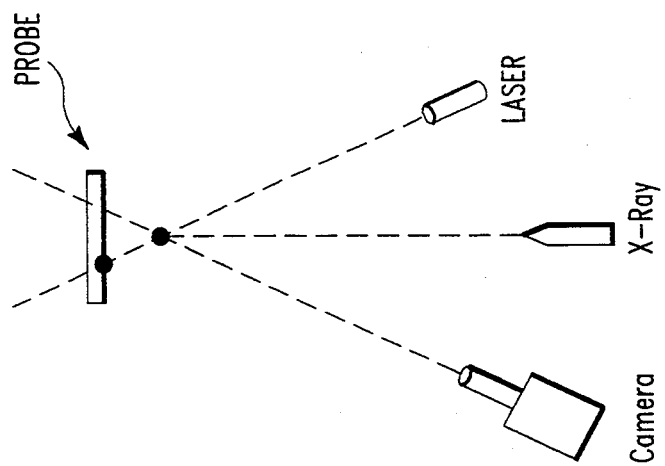
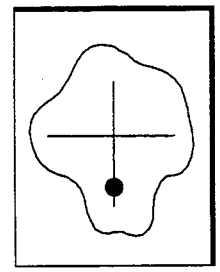
FIG. 4a
FIG. 4b
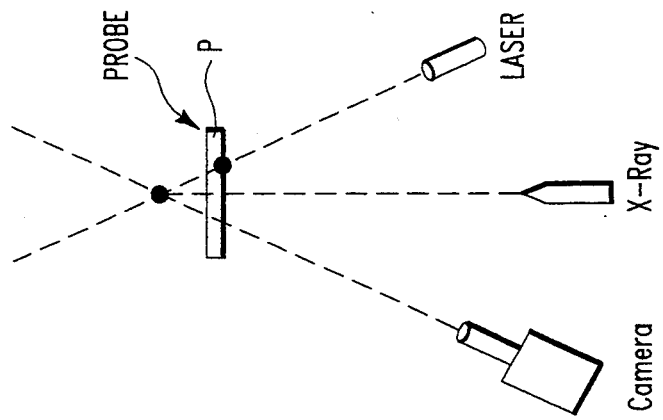
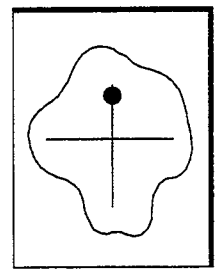
FIG. 5a
FIG. 5b

X-RAY MICRO DIFFRACTOMETER SAMPLE POSITIONER

FIELD OF THE INVENTION

This invention relates, to X-ray micro diffractometers and more particularly to a device for the accurate, reliable and simple positioning of the focal spot of the X-ray on the sample to be examined.

BACKGROUND OF THE INVENTION

It is known that X-ray diffractometers are very useful in analyzing certain materials. Generally, micro diffractometers are comprised of an emitter which generates an X-ray having a very small diameter, usually on the order of less than 50 μm. From an operational standpoint, the X-ray is used to illuminate specific points on the material to be examined. The X-ray which impinges upon the sample is scattered with the scattered radiation measured by means of a detector.

During the measurement process, the emitter and/or the sample and/or the detector are rotated around the zero point of the diffractometer. The zero point is that point which is located at the surface of the sample material which provides proper distance between the X-ray source, the sample and the detector, and is in effect the precise portion of the sample that is being examined. Generally, this spot is mathematically defined as that area which satisfies the relation $\theta$-/2-$\theta$ whereby $\theta$ is the angle of incidence between the X-ray and the sample.

Accordingly, in order to perform this analysis the X-ray must be very carefully positioned so as to be exactly on the surface point to be examined. Unfortunately, during analysis, X-ray radiation is both invisible to the human eye and hazardous to human health. Therefore, it is very difficult to properly align the sample sometimes requiring trial and error. Hence, as previously mentioned, the emitter and/or the sample and/or the detector are rotated during X-ray emission thereby insuring that proper alignment occurs at least occasionally during the evaluation. Accordingly, this has a tendency to require more time than is absolutely necessary, and will also generate more data, the bulk of which is irrelevant to the portion of the sample which is of interest.

Accordingly, it is an object of the present invention to produce an X-ray microdiffractometer which enables reliable and simple positioning of the focal spot of the X-ray on the sample. It is yet another object of the present invention to produce the aforementioned reliable and simple positioning while the focal spot lies in the zero point of the system.

It is yet another object of the present invention to produce a device which minimizes the amount of time required to irradiate the sample.

Still another object of the present invention is to produce a device which does not produce inordinate amounts of undesired or spurious data.

Finally another object of the present invention is to produce an X-ray microdiffractometer having a means for positioning a sample, a positionable X-ray emitter for generating a small diameter X-ray, a movable sample carrier for holding the sample and thereby moving the sample within three space coordinates, a detector positionable so as to be aimed at the zero point of the diffractometer while said X-ray emitter and the sample carrier are rotated around the zero point, a light source for generating a visible small diameter light beam, the light source aimable at the zero point, a camera having an optical axis, the camera aimable such that the optical axis passes through the zero point and forms an angle with the light beam of the light source so as to visibly indicate the zero point and the position of the sample with respect to the zero point.

BRIEF DESCRIPTION OF THE DRAWINGS

Reference may be now had to the accompanying drawings in which:

FIGS. 3a, 3b, 4a, 4b, 5a, 5b show the positioning of a sample according to the present invention where the sample is correctly located, behind the zero point and in front of the zero point respectively.

DETAILED DESCRIPTION. OF THE PREFERRED EMBODIMENT

Figure 1:
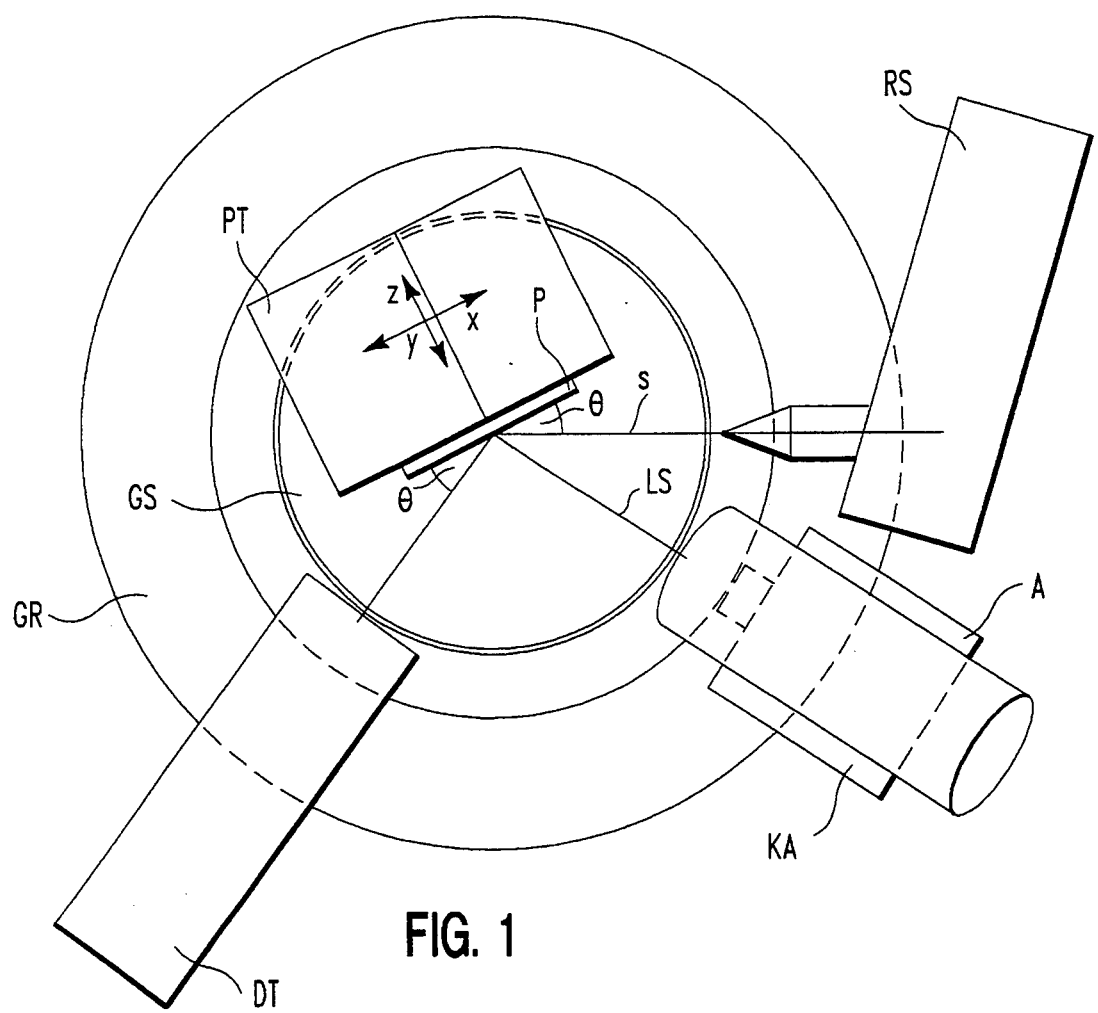
FIGS. 1 and 2 are block diagrams of the principle structure of an X-ray diffractometer according to the present invention.

Referring now to FIG. 1 there is shown a block diagram of the X-ray diffractometer of the present invention. Specifically, there is shown an X-ray emitter RS. X-ray emitter RS is of a type well known to one skilled in the art and is produced by a number of companies including the same assignee as the present invention. Emitter RS is used to aim a well directed X-ray S at an angle e which is then detected by the detector DT. Detector DT is attached to goniometer ring GR. Goniometer ring GR is used to move detector DT. It is to be understood that the configuration of X-ray emitter RS with respect to detector DT and goniometer ring GR is well known to one skilled in the art and is readily available. As such, a further detailed description of same is not deemed necessary at this point.

The sample P is clamped to an XYZ table PT wherein the table is located on an inner goniometric disk GS. Sample P is mounted such that it is moved not only in the three space coordinates X, Y, Z but is also rotatable around the center axis of the goniometer ring GR. Again, the XYZ table PT is readily known and available to one skilled in the art. The center axis of the table PT, when positioned properly, lies on the surface of sample P. Accordingly, the point at which the X-ray S and the axis of detector DT intersect is known as the zero point of the diffractometer.

By moving sample P in the X and Y direction, the surface of sample P may be analyzed on a point by point basis. By moving the sample P in the Z direction, the surface is effectively moved with respect to the zero point of the diffractometer. It has been observed that the point of impact of the X-ray S on the sample P, and thus the point to be examined by the X-ray should always be clearly recognizable so as to detect errors in positioning and measuring. Accordingly, a laser A and a camera, having an optical center axis KA, are utilized. The laser A is aligned such that a laser beam LS emanating from laser A passes through the zero point of the diffractometer. This laser beam LS also lies in the field of vision or shooting field of camera KA. It is to be understood that in the preferred embodiment of the present invention camera KA has imposed thereon cross hairs although other pointing mechanisms may be utilized such as, for example, a bulls eye.

As a result of the laser beam LS and the optical axis of the camera KA, a first angle is formed. Similarly, the X-ray emitter RS and the detector DT are located in one plane while the laser LS and the camera KA are located in a different plane with respect to each other. The intersection of these planes forms an angle $\theta$ which, in the preferred embodiment of the present invention, is an angle of 90° and at its intersection having common the zero point of the diffractometer. Accordingly, the plane formed by the camera KA and the laser LS intersects the other plane between the X-ray emitter RS and the detector DT while the zero point of the diffractometer lies at the intersection line.

Figure 2:
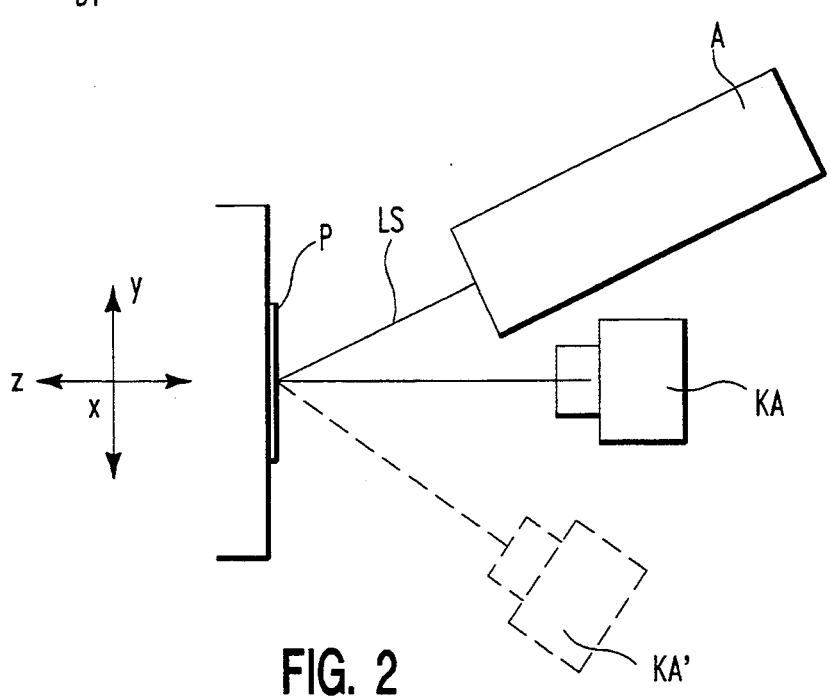

Referring now to FIG. 2 there is shown another block diagram of the X-ray diffractometer of the present invention illustrating two different orientations for exemplary purposes. Accordingly, shown is the camera KA which is aimed vertically at the sample P such that the overall sample surface is sharply imaged. However, in the event that the sample P has a highly reflective surface, the configuration shown by camera KA receives incoming light which is too weak. Accordingly, camera KA may be arranged so as to more effectively receive incoming light as shown by its orientation KA. In this case camera KA is purposely arranged at a reflection angle with respect to laser beam S, thereby indicating its versatility.

Referring now to FIGS. 3a and 3b there is respectively shown the orientation of the associated equipment and the image shot by the camera in diagrammatic form. Here it can be seen how cross hairs are superimposed on the image PB with respect to the sample and clearly indicates the zero point. More particularly, by positioning sample P appropriately, it in effect is positioned such that its surface lies in the zero point of the diffractometer such that the light spot generated by the laser LS on the sample P will appear on the monitor in the center of the cross hairs. Accordingly, the monitor image, therefore not only shows the point where the laser beam LS impacts a sample P but also the point of the impact of X-ray S. Also evident is how positioning of the cross hairs with respect to the zero point on the diffractometer can be performed both mechanically by aligning the camera and electronically by moving the cross hairs.

Referring now to FIGS. 4a and 4b there is shown a diagram similar to that of FIGS. 3a and 3b with the exception that the sample P is apart or removed from the X-ray emitters and the surface to be examined such that it appears to lie "behind" the zero point of the diffractometer. This therefore coincides with the sample being off axis with respect to the zero point. As a result, the laser beam LS on the X-ray RS impacts a different point on the sample. The result is that the light spot generated by the laser LS no longer appears at the center or cross point of the cross hairs of the monitor, but instead to the left. This therefore indicates to the user that the sample P must be moved "closer" in the Z direction and perhaps adjusted in one or more coordinates.

Referring now to FIGS. 5a and 5b there is again shown a diagram similar to that of FIGS. 3a, 3b, 4a, and 4b with the difference being the sample P appearing to be located in "front" of the zero point of the diffractometer. Accordingly, with this setting or positioning of the sample P, the light spot generated by the laser LS appears to be to the right of the cross hairs. Again, appropriate correction or repositioning of the sample will properly align the sample with respect to the cross hairs thereby indicating correct zero point intersections.

It is to be understood that although the relative angles of the camera and laser with respect to each other are as shown, it is to be understood that the greater the angle between the laser beam LS and the camera axis KA, the more sensitive the display of the correct positioning of the X-ray RS will be.

Accordingly, with the diffractometer of the present invention it can be readily seen how one can determine, at a safe distance from the X-ray radiation RS, whether the surface of the sample lies at the zero point, in front or after it. Therefore, by setting the correct distance, the sample can now be so moved in the X-Y direction and the desired point can thus be easily examined. As an added advantage or feature, during the entire analysis, the user can monitor the desired setting.

It is to be understood that many variations of the present invention may be practiced without departing from the spirit and scope of the present invention. For example, any reasonable suitable type of camera may be utilized while different types of light sources could be utilized. Additionally, the mechanism for adjustment of the sample can be changed without departing from the spirit and scope of the present invention.

What is claimed is:

1. An X-ray microdiffractometer having a means for positioning a sample, comprising:
    a positionable X-ray emitter (RQ) for generating a small diameter X-ray;
    a movable sample carrier (PT) for holding the sample (P) and thereby moving said sample within three space coordinates;
    a detector (DT) positionable so as to be aimed at the zero point of the diffractometer while said X-ray emitter (RQ) and said sample carrier (PT) are rotated around the zero point;
    a light source (LA) for generating a visible small diameter light beam, said light source aimable at the zero point; and
    a camera (KA) having an optical axis, said camera aimable such that said optical axis passes through the zero point and forms an angle with said light beam of said light source (LA) so as to visibly indicate the zero point and the position of the sample with respect to the zero point.

2. A device according to claim 1 wherein said angle between said optical axis of said camera and said light beam is in the range of 45° through 160°.

3. A device according to claim 1 wherein said camera has an optical viewing field discernable by a user, said viewing field having locating indicia thereon.

4. A device according to claim 1 wherein said angle between said optical axis of camera and said laser beam forms a first plane, the angle between said X-ray emitter and said detector are disposed at an angle with respect to each other so as to form a second plane and wherein said first plane and said second plane are disposed with respect to each other at an angle greater than zero.

5. A device according to claim 4 wherein said first plane and said second plane intersect at said zero point so as to form an angle therebetween.

6. A device according to claim 5 wherein said angle between said first and said second plane is in the range of 45° through 160°.

* * * * *